United States Patent
Lee et al.

(10) Patent No.: US 8,450,684 B2
(45) Date of Patent: May 28, 2013

(54) QUANTIFICATION METHOD OF FUNCTIONAL GROUPS OF ORGANIC LAYER

(75) Inventors: Tae Geol Lee, Daejeon (KR); Dae Won Moon, Daejeon (KR); Hyegeun Min, Daejeon (KR)

(73) Assignee: Korea Research Institute of Standards and Science (KR)

( * ) Notice: Subject to any disclaimer, the term of this patent is extended or adjusted under 35 U.S.C. 154(b) by 304 days.

(21) Appl. No.: 13/063,616

(22) PCT Filed: Sep. 24, 2009

(86) PCT No.: PCT/KR2009/005454
§ 371 (c)(1),
(2), (4) Date: Mar. 11, 2011

(87) PCT Pub. No.: WO2010/036038
PCT Pub. Date: Apr. 1, 2010

(65) Prior Publication Data
US 2011/0163228 A1     Jul. 7, 2011

(30) Foreign Application Priority Data

Sep. 26, 2008   (KR) ................. 10-2008-0094625
Sep. 24, 2009   (KR) ................. 10-2009-0090385

(51) Int. Cl.
*G01N 23/203*     (2006.01)
(52) U.S. Cl.
USPC ................... 250/307; 250/305; 250/309
(58) Field of Classification Search
CPC .............................................. H01J 2237/2804
USPC .................... 250/305, 307, 309; 702/28
See application file for complete search history.

(56) References Cited

U.S. PATENT DOCUMENTS

| | | | |
|---|---|---|---|
| 5,923,119 | A | 7/1999 | Hara et al. |
| 2002/0160227 | A1 | 10/2002 | Kohama et al. |
| 2006/0083947 | A1 | 4/2006 | Ikeda et al. |
| 2006/0246302 | A1* | 11/2006 | Brady et al. ............ 428/441 |

OTHER PUBLICATIONS

Moon et al., 'Medium-Energy Ion Scattering Spectroscopy for Quantitative Surface and Near-Surface Analysis of Ultrathin Films', Aug. 2000, Surface and Interface Analysis, vol. 30, Issue 1, p. 484-487.*
Hyegeun Min et al., "MEIS and ToF-SIMS analyses of organic ultrathin films for absolute quantification of functional groups," Surf. Interface Anal., vol. 43, 2011, pp. 393-396.
International Search Report—PCT/KR2009/005454 dated May 25, 2011.

* cited by examiner

*Primary Examiner* — Jack Berman
*Assistant Examiner* — Eliza Osenbaugh-Stewart
(74) *Attorney, Agent, or Firm* — Cantor Colburn LLP (57) ABSTRACT

A quantification method of functional groups in an organic thin layer includes: a) measuring an absolute quantity per unit area of an analysis reference material having functional groups included in a reference organic thin layer by means of MEIS spectroscopy; b) carrying out spectrometry for the same reference organic thin layer as in a) and thereby obtaining peak intensities of the functional groups in the reference organic thin layer; c) carrying out the same spectrometry as in b) for an organic thin layer to be analyzed having the same functional groups and thereby measuring peak intensities of the functional groups with unknown quantity; and d) comparing the peak intensities of the functional groups measured in b) with respect to the absolute quantity of the analysis reference material in a) and thereby determining the absolute quantity per unit area of the functional groups with unknown quantity measured in c).

10 Claims, 7 Drawing Sheets

QUANTIFICATION METHOD OF FUNCTIONAL GROUPS OF ORGANIC LAYER

TECHNICAL FIELD

The present invention relates to a quantification method of functional groups of a material included in an organic thin layer.

BACKGROUND ART

Recently, applications of organic and bio thin films in areas such as flexible displays, solar cells, organic sensors, biomaterials, biochips, and the like have been intensely studied. The performance of these films in terms of biomaterial sensing and biocompatibility is mainly determined by surface functional groups, and as such, to increase performance of the organic and bio thin films, quantitative determination of the surface functional groups is important. However, in spite of many researches carried out thus far, these efforts have been unsuccessful because of the difficulty of determining the relative sensitivity factors (RSFs) of the functional groups. For example, the RSF values of the various functional groups on organic and bio thin films are not known yet despite the molecular chemical information on the surface functional groups that x-ray photoelectron spectroscopy (XPS) provides. Other techniques, such as Fourier transform-infrared (FT-IR) spectroscopy and secondary ion mass spectrometry (SIMS), that are widely used for chemical analysis of organic and bio thin films are also inadequate for producing a quantitative analysis of surface functional groups.

DISCLOSURE OF INVENTION

Technical Problem

The inventors of the present invention have noticed that references not affected by relative sensitivity factors (RSFs) are required for quantification of functional groups on an organic thin layer and that medium energy ion scattering (MEIS) spectroscopy is adequate for the purpose. The MEIS spectroscopy is effective in determining the composition of a thin film formed on a silicon oxide ($SiO_2$) layer with a resolution of a single atomic layer. If the result is normalized by the surface density of Si of a known silicon oxide layer, the absolute surface density of a wanted element can be determined. Then, calibration factors (CFs) for the elements of the functional groups may be computed from the XPS intensities. This can be applied to other surface analysis techniques such as Fourier transform-infrared (FT-IR) spectroscopy and secondary ion mass spectrometry (SIMS).

Accordingly, an object of the present invention is to provide a quantification method of functional groups of a material included in an organic thin layer, specifically a method of absolutely quantifying the number of molecules in a material in an organic thin film by measuring the density of reference elements by means of medium energy ion scattering (MEIS) spectroscopy followed quantifying the functional groups on the organic thin layer relative to the references by means of x-ray photoelectron spectroscopy (XPS), Fourier transform-infrared (FT-IR) spectroscopy or time-of-flight secondary ion mass spectrometry (ToF-SIMS).

Solution to Problem

In an aspect, the present invention provides a quantification method of functional groups in an organic thin layer comprising: a) measuring an absolute quantity per unit area of an analysis reference material having functional groups included in a reference organic thin layer by means of medium energy ion scattering (MEIS) spectroscopy; b) carrying out spectrometry for the same reference organic thin layer as in a) and thereby obtaining peak intensities of the functional groups in the reference organic thin layer; c) carrying out the same spectrometry as in b) for an organic thin layer to be analyzed having the same functional groups as those included in the analysis reference material of a) and thereby measuring peak intensities of the functional groups with unknown quantity; and d) comparing the peak intensities of the functional groups measured in b) with respect to the absolute quantity of the analysis reference material in a) and thereby determining the absolute quantity per unit area of the functional groups with unknown quantity in the organic thin layer to be analyzed measured in c).

In another aspect, the present invention provides a quantification method of functional groups in an organic thin layer comprising: e) carrying out spectrometry for an organic thin layer to be analyzed and thereby obtaining peak intensities of functional groups with unknown quantity; and f) comparing the peak intensities of the functional groups with unknown quantity obtained in e) with respect to an absolute quantity per unit area of functional groups included in a reference organic thin layer, which is obtained by comparing an absolute quantity per unit area of an analysis reference material having functional groups included in the reference organic thin layer measured by means of MEIS with peak intensities of the functional groups in the reference organic thin layer measured by means of spectrometry, and thereby determining the absolute quantity per unit area of the functional groups in the organic thin layer to be analyzed.

The absolute quantity per unit area of the functional groups in the organic thin layer measured in a), b) or f) may be used as Certified Reference Material (CRM) to obtain the absolute quantity per unit area of the same functional groups on a new organic thin layer to be analyzed.

The reference organic thin layer is prepared by spin-coating organic thin layers with different concentrations, which are prepared from an analyte including the analysis reference material at various concentrations, on a monocrystalline silica substrate, a monocrystalline silicon substrate having a surface oxide layer or a monocrystalline silicon substrate.

The spectrometry may be X-ray photoelectron spectroscopy (XPS), Fourier transform-infrared (FT-IR) spectroscopy or time-of-flight secondary ion mass spectrometry (ToF-SIMS), but not limited thereto.

The measurement of the absolute quantity per unit area of the analysis reference material having functional groups included in the reference organic thin layer by means of MEIS may comprise: i) injecting protons ($H^+$) along a crystal direction of the reference organic thin layer on a predetermined area of the reference organic thin layer and detecting the energy and emission quantity of the scattered protons; ii) obtaining the areal density of elements based on the detected energy and emission quantity of the protons; and iii) obtaining the density of the analysis reference material from the areal density of the elements included in the reference organic thin layer.

In iii), the areal density of elements included in the functional groups of the reference organic thin layer is obtained from the areal density of the analysis reference material.

Advantageous Effects of Invention

The quantification method of functional groups in an organic thin layer according to the present invention is an absolute quantification method. A sample of which the absolute density of an organic thin layer and an absolute density of the functional groups in the organic thin layer have been measured may be used as a Certified Reference Material (CRM) for an absolute quantification of organic thin layers.

Further, through quantification of the density of functional groups in an organic thin layer, the quantification method of the present invention allows the manufacture of an organic thin layer enabling quality control, and thereby remarkably improves performance and reliability.

BRIEF DESCRIPTION OF DRAWINGS

The above and other objects, features and advantages of the present invention will become apparent from the following description of preferred embodiments given in conjunction with the accompanying drawings, in which.

MODE FOR THE INVENTION

Hereinafter, the embodiments of the present invention will be described in detail with reference to accompanying drawings. The following embodiments are for illustrative purposes only and not intended to limit the scope of the present invention. Therefore, the present invention may be embodied in a different manner.

Unless otherwise defined, all terms (including technical and scientific terms) have the same meaning as commonly understood by one of ordinary skill in the art. In the following description and drawings, details of well-known features and techniques may be omitted to avoid unnecessarily obscuring the present invention.

PREPARATION EXAMPLE 1

Preparation of Organic Thin Layer by Spin-coating

A Ru 535-bis TBA dye represented by Chemical Formula 1 [cis-bis(isothiocyanato)bis(2,2'-bipyridyl-4,4'-dicarboxylato)-ruthenium(II)bis-tertabutylammonium; $C_{58}H_{86}O_8N_8S_2Ru$; hereinafter, Ru 535-bis TBA] was purchased from Solaronix SA. The Ru 535-bis TBA dye was dissolved in ethanol solvent at concentrations of 5 mM, 2.5 mM, 1 mM, 0.5 mM, 0.25 mM and 0.1 mM for X-ray photoelectron spectroscopy (XPS) and Fourier transform-infrared (FT-IR) spectroscopy measurements, and at 0.01 mM, 0.005 mM, 0.0025 mM and 0.001 mM for time-of-flight secondary ion mass spectrometry (ToF-SIMS) measurement.

A 500 µL droplet of ethanol solution each containing Ru 535-bis TBA with different concentration was dropped on a silicon wafer that had been cleaned with a super-piranha solution [according to the method presented on-line in H. Min, J.-W. Park, H. K. Shon, D. W. Moon, T. G. Lee, *Appl. Surf Sci.* (2008)]. Then, a homogeneous organic thin layer was formed by spin-coating at 5000 rpm for 20 seconds.

[Chemical Formula 1]

Chemical structure of cis-bis(isothiocyanato)bis(2,2'-bipyridyl-4,4'-dicarboxylato)-ruthenium(II)bis-tertabutylammonium (Ru 535-bis TBA; $C_{58}H_{86}O_8N_8S_2Ru$) dye formed on silicon substrate Experimental Procedure 1. MEIS Analysis Medium energy ion scattering (MEIS) spectroscopy, a low-energy version of ion scattering spectroscopy, was used for absolute quantification of elemental composition of a thin layer formed on a silicon or silicon oxide substrate with a depth resolution of 10 or less. An MEIS system at the Korea Research Institute of Standards and Science (KRISS) was used. The energy loss of proton ($H^+$) beams accelerated at 100 keV after being scattered from a sample was in the range of several hundred eV/nm and could be measured precisely with an energy resolution of about 0.1%, which corresponded to a depth resolution of a single atomic layer.

The incident ions were along the [111] direction in the (011) plane, and the scattered ions were along the [00ī] direction with a scattering angle of 125°. By using the ion scattering simulation program by Kido, depth profiles of elements in each layer were obtained from the MEIS spectra.

2. XPS Analysis

XPS spectra were obtained using ESCA, SIGMA PROBE (ThermoVG, U.K.) of the National Center for Inter-University Research Facilities at Seoul National University. 100 W monochromatic Al—$K_\alpha$ was used as X-ray source.

3. FT-IR Analysis

Absorption spectra for the Ru thin layer on silicon surface were measured with a Thermo Nicolet FT-IR spectrometer (Nexus 6700). Ru 535 bis-TBA solution was spincoated on both sides of a silicon wafer. IR beam was irradiated vertically on the surface of the silicon substrate, which was cut to 55×10×0.6 mm$^3$, beveled to be parallel at 45° and minor-polished, so that the beam could be internally reflected at least 18 times in the silicon crystal (Si(100)). Measurement was made using a liquid nitrogen-cooled mercury-cadmium-telluride (MCT-A) detector. All spectra were averaged at 128 scans with 4 cm$^{-1}$ resolution under a stream of nitrogen gas.

4. ToF-SIMS Analysis

ToF-SIMS spectra were obtained by irradiating Bi$^+$ primary ions at 25 keV using a ToF-SIMS V apparatus (ION-TOF GmbH, Germany). Average current of primary ion source was 0.36 pA. Cycle period was 200 μs. Measurement area was 200×200 μm$^2$, and primary ion dose was $10^{12}$ ions/cm$^2$. for $CH_3^+$, $C_2H_3^+C_3H_5^+$ for $CH^-$, $C_2H^-$ and $C_4H^-$ ions.

EXAMPLE 1

Figure 1:
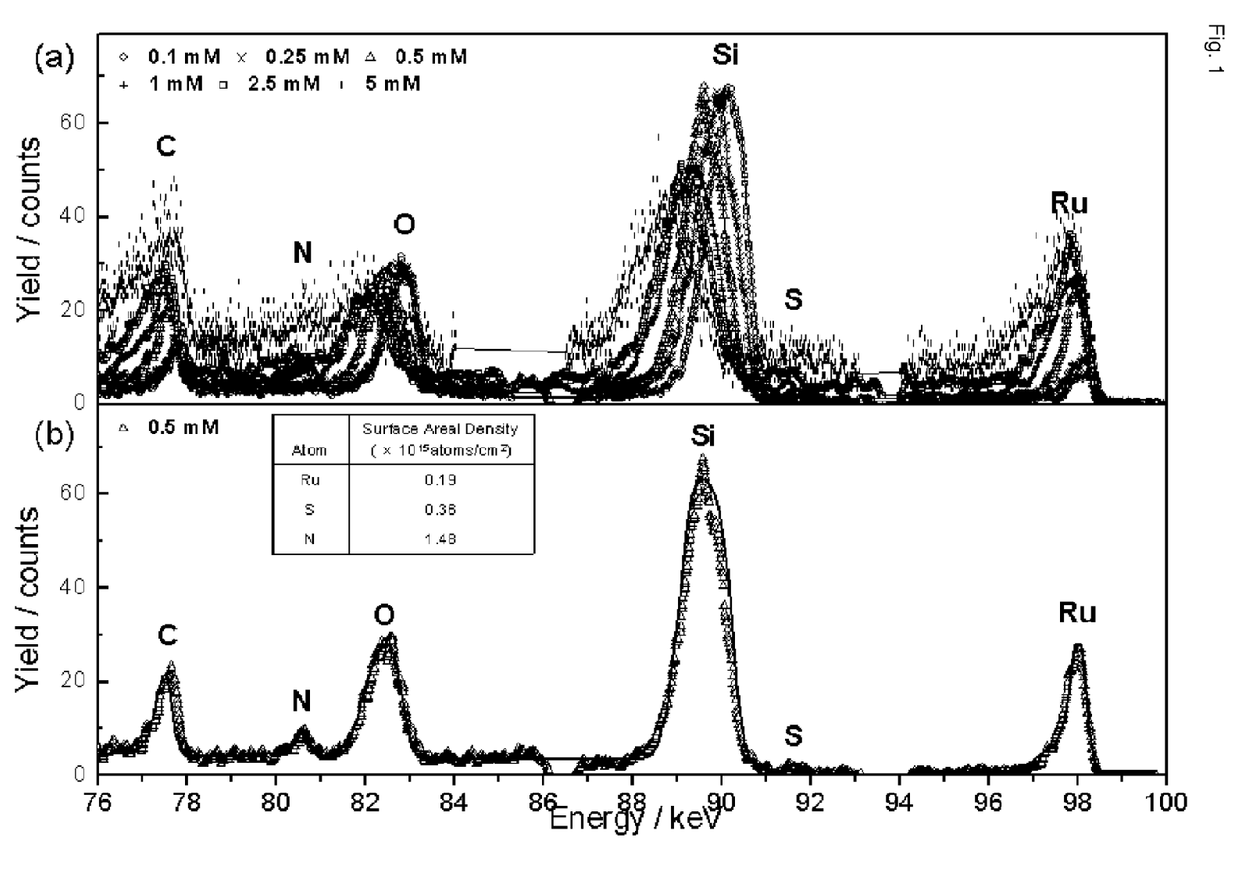
FIG. 1 shows medium energy ion scattering (MEIS) spectra for Ru dye thin layers with different concentrations obtained in Example 1.

The organic thin layers prepared at concentrations of 5 mM, 2.5 mM, 1 mM, 0.5 mM, 0.25 mM and 0.1 mM in Preparation Example 1 were analyzed by means of MEIS. FIG. 1 (a) shows MEIS spectra for the organic thin layers produced by spin-coating ethanol solutions of Ru 535-bis TBA dye with different concentrations onto silicon substrates. FIG. 1 (b) shows MEIS spectrum and simulated fitting line of the 0.5 mM thin layer as a typical example.

FIG. 1 shows MEIS spectra for the Ru dye thin layers with different concentrations obtained in Example 1. In FIG. 1, the areas under the C, N, O, Si, S and Ru peaks mean their areal density. The total quantity of each element can be obtained by computing the quantity of H$^+$ emitted with different energies from each slab of the sample by means of Kido simulation. The larger the concentration, the larger the density and thickness of the Ru dye layer are. At concentrations 2.5 mM or higher, the peaks showed thick and long tails due to severe clustering.

Because Ru metal is highly sensitive to MEIS measurement, the density of the element can be exactly computed through simulation. The density is also the absolute quantity of the Ru 535-bis TBA molecules present in the thin layer. A method for absolute quantification of the number of molecules in an organic thin layer by means of MEIS analysis is described in detail in Korean Patent Application No. 2008-0081887.

Table 1 shows densities of Ru at different concentrations. The average size of the Ru 535-bis TBA molecule represented by Chemical Formula 1 is about 1.6 nm, which was estimated by a molecular mechanics simulation. Based on the molecule size, the density of a monolayer was calculated to be $1/1.6^2$ nm$^2$=$0.039\times10^{15}$ cm$^{-2}$. The thicknesses of the Ru dye thin layers prepared by spin-coating were computed from the result and are presented in Table 1.

TABLE 1

| Concentration/ mM | Ru Density/ $\times10^{15}$ cm$^{-2}$ | Number of Layers* | Thickness**/ nm | |
|---|---|---|---|---|
| 0.10 | 0.05 | ~1 | ~2.0 | Monolayer |
| 0.25 | 0.07 | ~2 | ~2.8 | Multilayer |
| 0.50 | 0.19 | ~5 | ~7.6 | Multilayer |
| 1.00 | 0.26 | ~7 | ~10.4 | Multilayer |
| 2.50 | 0.38 | ~10 | ~15.2 | 3D Island |
| 5.00 | 0.56 | ~14 | ~22.4 | 3D Island |

EXAMPLE 2

MEIS analysis was carried out in the same manner as Example 1 for the organic thin layers prepared in Preparation Example 1. XPS peak intensities of functional groups with different concentrations on the organic thin layers the same as those prepared in Preparation Example 1 were measured.

Figure 2:
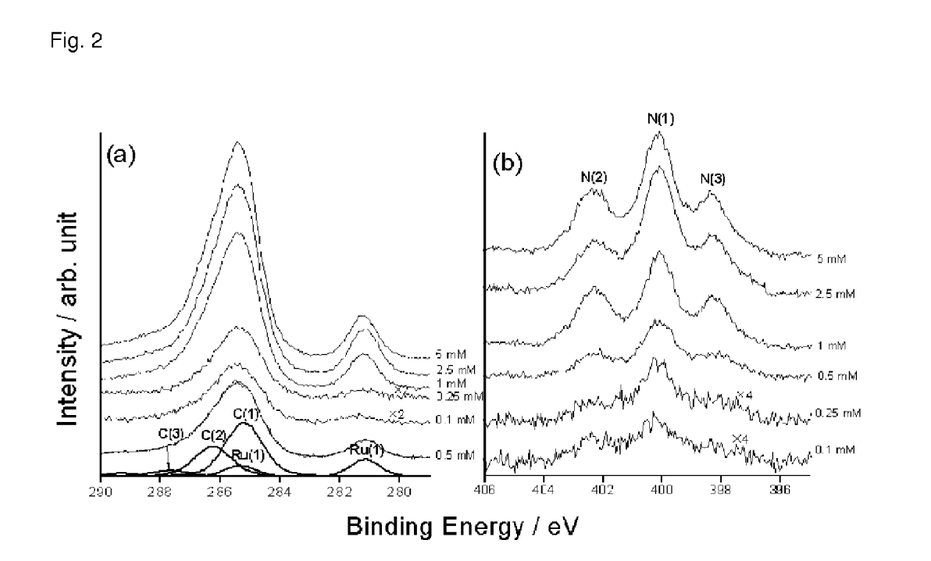
FIG. 2 shows X-ray photoelectron spectroscopy (XPS) spectra obtained in Example 2.

FIG. 2 shows the XPS spectra obtained in Example 2. In FIG. 2, (a) shows C 1s, Ru 3d spectra and (b) shows N 1s spectra. The Ru 3d band was branched into Ru $3d_{5/2}$ and Ru $3d_{3/2}$ by spin-orbit splitting. The C 1s peak was deconvoluted into three C peaks originating from C—C, CN (or NCS) and COO band peaks, as seen in the molecular structure of Ru 535-bis TBA. Also, N 1s had three peaks corresponding to $C_4N$, $C_2NRu$ and CNRu peaks.

The XPS spectra peak intensities were fitted against absolute density of Ru at different concentrations obtained from MEIS.

Figure 3:
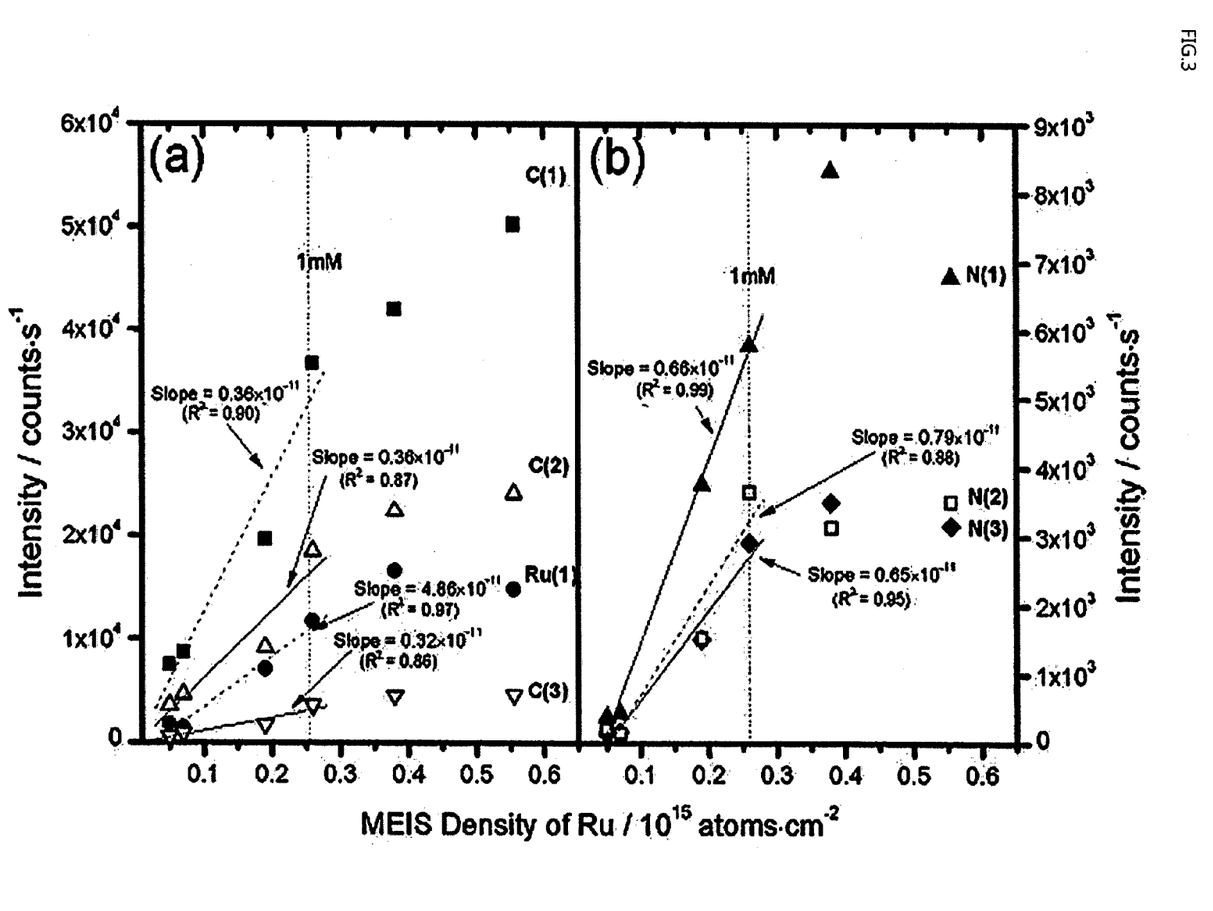
FIG. 3 shows XPS intensities of functional groups obtained in Example 2 with respect to the Ru absolute quantity. (a): Ru $3d_{5/2}$, C 1s, and (b): N 1s.

FIG. 3 shows XPS intensities of Ru $3d_{5/2}$, C 1s (a), and N 1s (b) obtained in Example 2 with respect to the Ru absolute quantity. FIG. 3 (a) is a fitting plot of XPS intensities of Ru $3d_{5/2}$ originating from $N_6Ru$ and C 1s peaks, and FIG. 3 (b) is a fitting plot of XPS intensities of N 1s peak, against Ru density.

As seen from FIGS. 3 (a) and (b), XPS peak intensities increased with the increase of Ru density until the saturation at $0.38\times10^{15}$ atoms/cm$^2$, which corresponds to a concentration of 2.5 mM. Accordingly, RSFs (relative sensitivity factors) of the elements in the functional groups were obtained from the slopes in the region where the XPS intensities increase linearly. From the slopes of the graphs in FIGS. 3 (a) and (b), calibration factors (CFs) were calculated according to the following equation, and the result is summarized in Table 2.

$$CF_a = \frac{XPS \text{ intensity}}{A \text{ real density of functional group}} = \frac{slope_a}{N_a}$$

Table 2 shows the CF values obtained from FIGS. 3 (a) and (b), concentrations of Ru, C and N in the functional groups of 0.5 mM thin layers calculated therefrom, and stoichiometric fractions in a Ru 535-bis TBA molecule ($C_{58}H_{86}O_8N_8S_2Ru$).

TABLE 2

| XPS Atomic Bands | Functional Groups | | Calibration Factors (CFs)/×10$^{-11}$ counts·cm$^2$·atoms$^{-1}$·s$^{-1}$ | Concentration (%) calculated by CF | Stoichiometric Fraction (%) |
|---|---|---|---|---|---|
| Ru 3d | Ru(1) | N$_6$Ru | 4.86 | 1.52 | 1.49 |
| C1s | C(1) | C—C | 0.36 | 56.73 | 53.73 |
|  | C(2) | CN$_1$ NCS | 0.36 | 26.53 | 26.87 |
|  | C(3) | COO | 0.32 | 5.61 | 5.97 |
| N1s | N(1) | C$_2$NRu | 0.66 | 5.87 | 5.97 |
|  | N(2) | C$_1$N$^+$ | 0.79 | 1.93 | 2.99 |
|  | N(3) | NCS | 0.65 | 2.39 | 2.99 |
|  |  | Total |  | 100 | 100 |

With the CF values, the surface density of the functional groups could be obtained from the XPS intensities.

EXAMPLE 3

MEIS analysis was carried out in the same manner as Example 1 for the organic thin layers prepared in Preparation Example 1. FT-IR peak intensities of functional groups with different concentrations on the organic thin layers the same as those prepared in Preparation Example 1 were measured.

Figure 4:
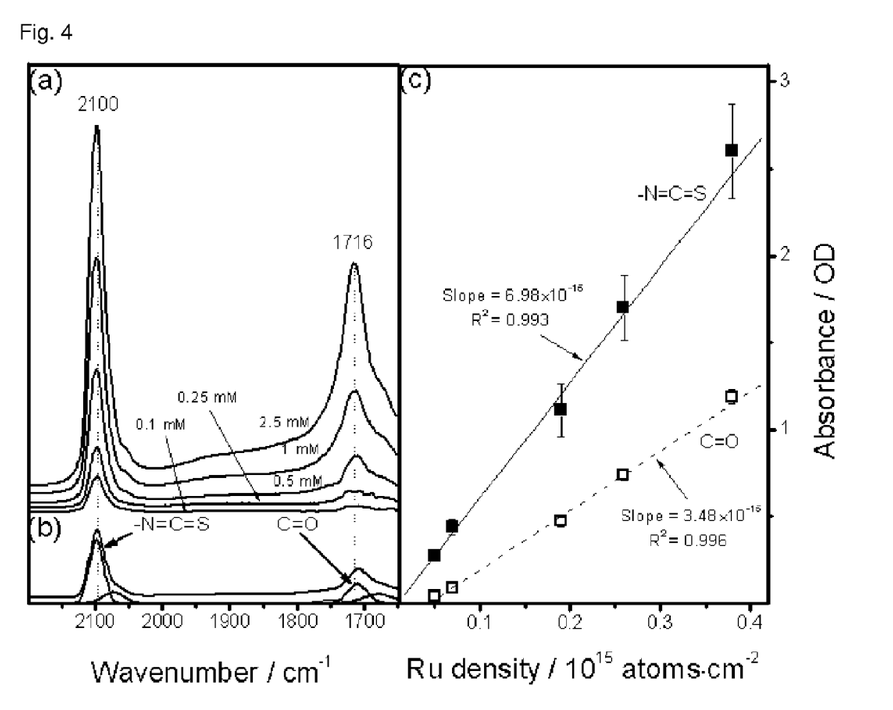
FIG. 4 shows Fourier transform-infrared (FT-IR) spectra of Ru thin layers with different concentrations and FT-IR vibration peak intensities of $v_{as}$(—N═C═S) and $v_{as}$(C═O) with respect to the Ru absolute quantity.

FIG. 4 (a) shows FT-IR spectra of the Ru thin layers with different concentrations. From the deconvoluted peaks of FIG. 4 (b), $\nu_{as}$(—N=C=S) and $\nu_{as}$(C=O) vibration peaks are seen, with the intensities varying clearly depending on concentrations.

FIG. 4 (c) shows normalized $\nu_{as}$(—N=C=S) and $\nu_{as}$(C=O) vibration peak intensities against the Ru absolute quantity. As seen in FIG. 4 (c), a linearity is seen. Since the Ru compound has two NCS functional groups and four COO groups, as seen in Chemical Formula 1, FT-IR CFs for the NCS and COO groups are calculated to be 3.49×10$^{-15}$ OD·cm$^2$·atoms$^{-1}$ and 0.87×10$^{-15}$ OD·cm$^2$·atoms$^{-1}$, respectively, as in Example 2.

EXAMPLE 4

ToF-SIMS peak intensities of functional groups with concentrations of 0.01 mM, 0.005 mM, 0.0025 mM and 0.001 mM on the organic thin layers the same as those prepared in Preparation Example 1 were measured.

Figure 5:
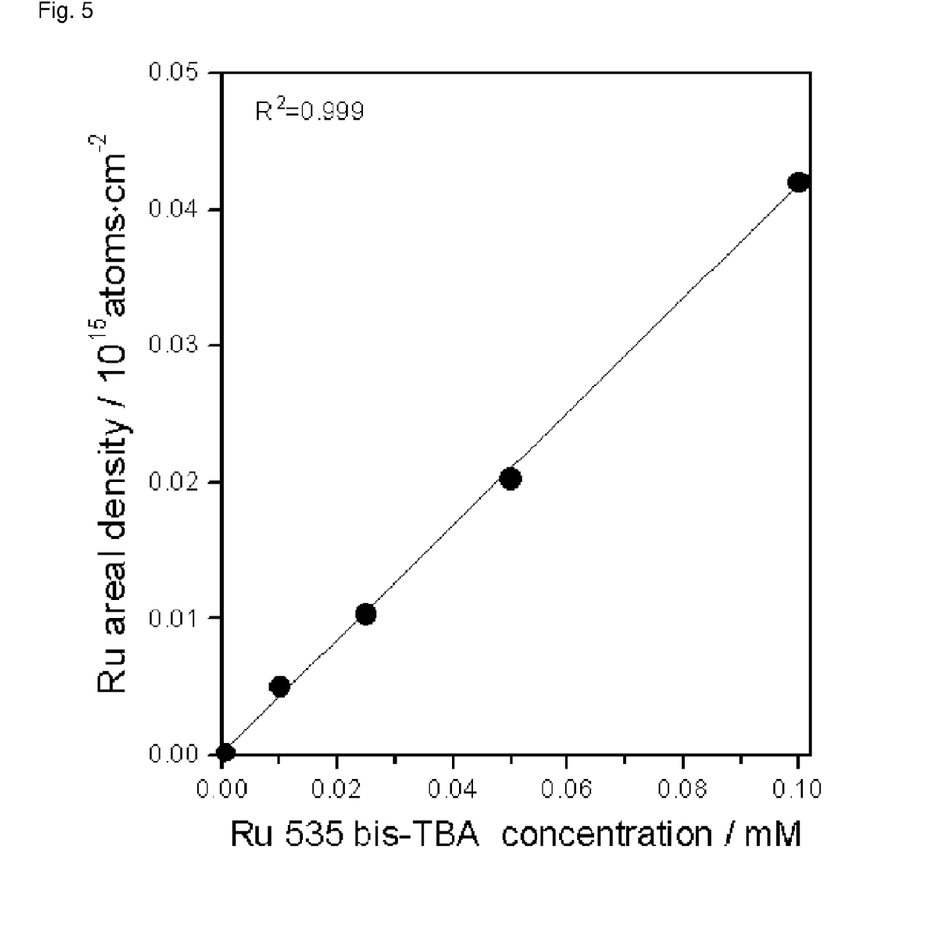
FIG. 5 shows Ru surface density at different concentrations obtained in Example 4 from MEIS spectra.

FIG. 5 shows the densities of the organic thin layers obtained from MEIS spectra.

Since the density of the Ru dye thin layer with the concentration 0.01 mM is 0.042×10$^{-15}$ atoms·cm$^{-2}$, the thickness of the monolayer is calculated as 1.7 nm from the density of the monolayer 0.039×10$^{-15}$ atoms·cm$^{-2}$ obtained in Example 1. Therefore, ToF-SIMS analysis with a detection limit of 2 nm or smaller is applicable to the quantification of organic thin layers with concentrations 0.01 mM or less.

Figure 6:
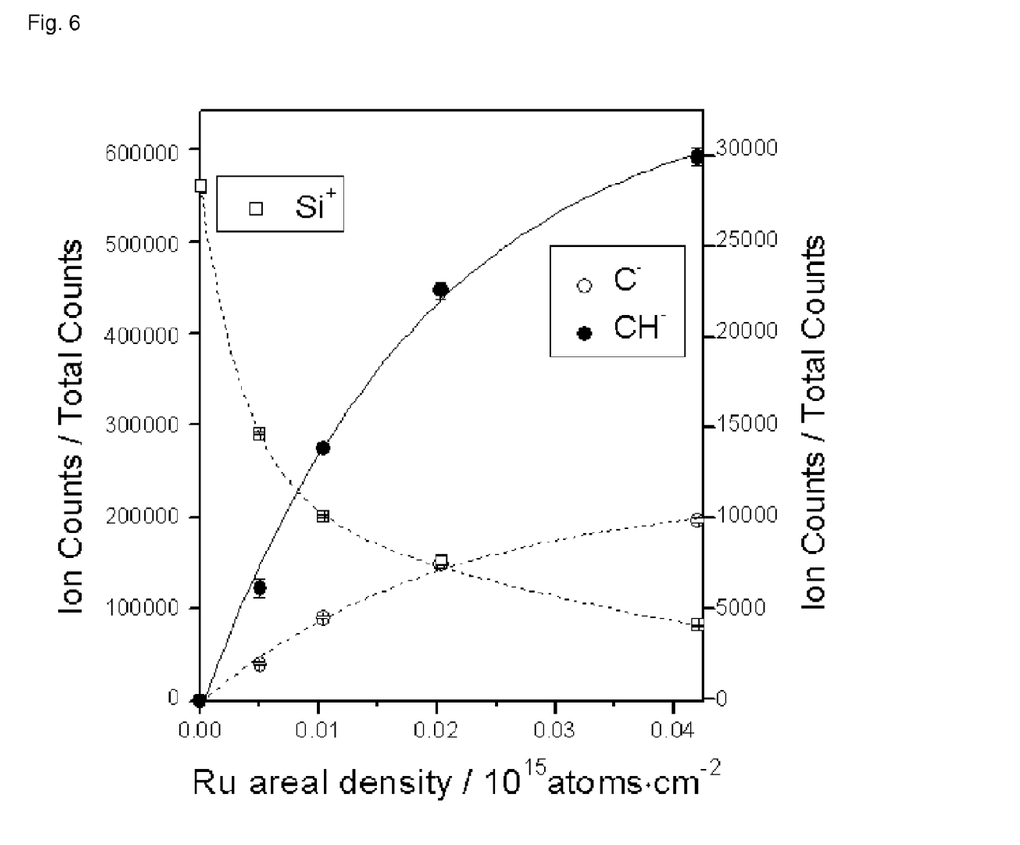
FIG. 6 shows $C^-$, $CH^-$ and $Si^+$ peak intensities measured by means of time-of-flight secondary ion mass spectrometry (ToF-SIMS) plotted against the Ru surface density obtained from MEIS.
Figure 7:
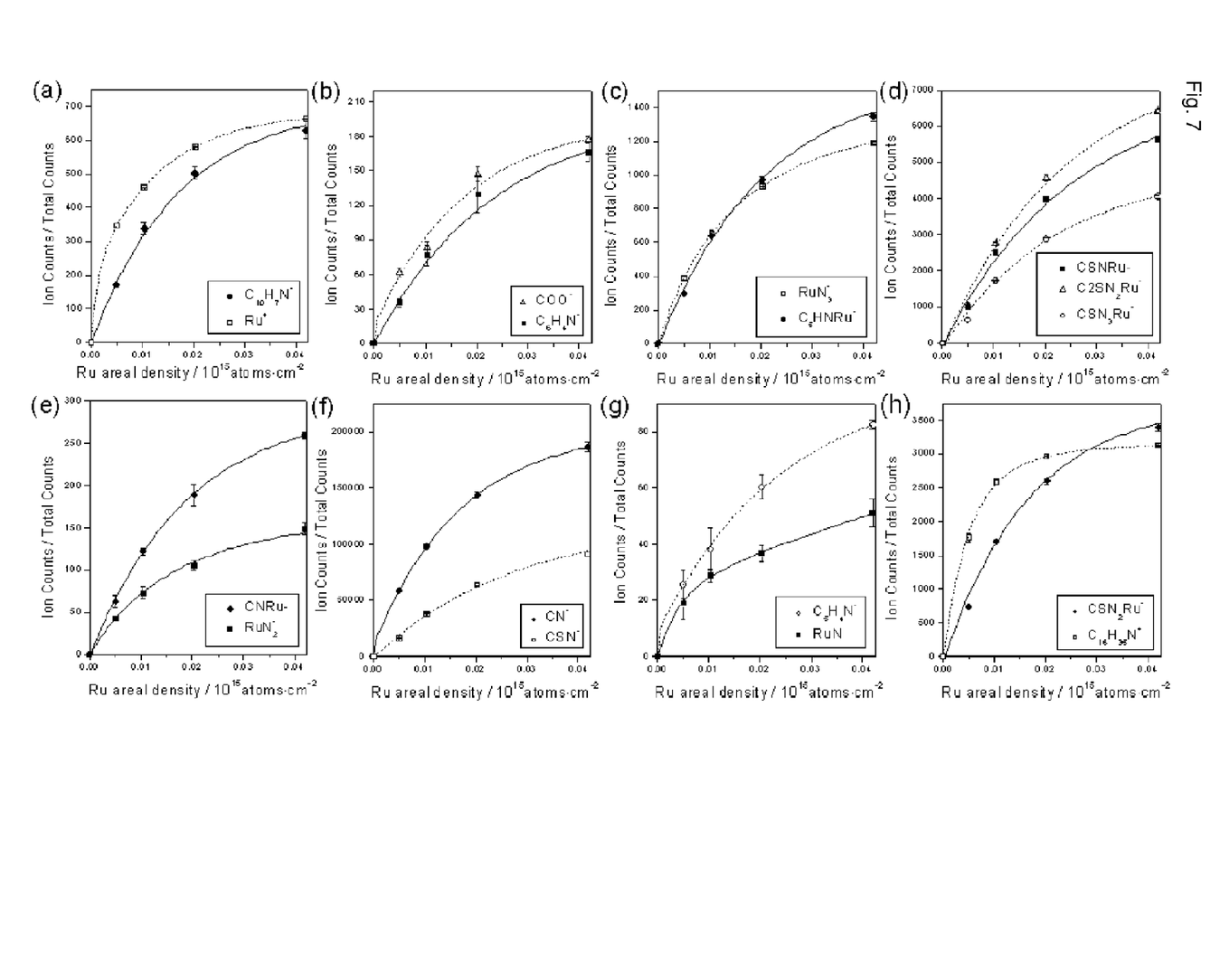
FIG. 7 shows fragment peak intensities measured by means of ToF-SIMS plotted against the Ru surface density.

FIG. 6 shows C$^-$, CH$^-$ and Si$^+$ peak intensities measured by means of ToF-SIMS plotted against the Ru surface density obtained from MEIS. It can be seen that the C$^-$ and CH$^-$ peaks increase exponentially, whereas the Si$^+$ peak decreases exponentially. Similarly, FIG. 7 shows fragment peak intensities of the functional groups of Ru 535-bis TBA. The peak intensities show exponential, not linear, tendencies depending on the density of the Ru dye thin layer, because of the matrix effect. Although the peaks show different increasing patterns due to the difference in secondary ion formation, all of them can be expressed by the following exponential functions.

$$y = A_1 \exp(-x/t_1) + A_2 \exp(-x/t_2) + A_3 \exp(-x/t_3) + y_0$$

Accordingly, once the constants $A_1, A_2, A_3, t_1, t_2, t_3$ and $y_0$ for each peak are determined, the surface density of functional groups of similar organic thin layers can be easily obtained only with ToF-SIMS measurements.

As demonstrated through Examples 1 to 4, the functional groups of Ru dye complex organic thin layers formed by spin-coating can be quantified through a surface analysis using MEIS, XPS, FT-IR and ToF-SIMS. Further, it is possible to develop CRMs absolutely quantified for each functional group.

Furthermore, it is possible to control the density and thickness of thin layers by varying the concentration of the spin-coating solution of Ru 535 bis-TBA, which is known to provide high efficiency in dye-sensitized solar cells.

The quantification method of functional groups according to the present invention enables an absolute quantification of the molecule number of Ru 535 bis-TBA in a thin layer by measuring the density of Ru by means of medium energy ion scattering (MEIS) spectroscopy. The result can be presented as references for surface analysis techniques, such as X-ray photoelectron spectroscopy (XPS), Fourier transform-infrared (FT-IR) spectroscopy and time-of-flight secondary ion mass spectrometry (ToF-SIMS). Calibration factors (CFs) for XPS may be applied to quantification of other organic thin layers including functional groups with unknown quantity. Further, the quantification method may be extended to a development of a quantification method of functional groups on organic thin layers utilizing other analysis techniques, without being limited to XPS, FT-IR and ToF-SIMS. The quantification method of functional groups on an organic thin layer according to the present invention enables the quantification of organic thin layers of great industrial importance in various fields and is expected to improve performance and reliability. Further, by using the Certified Reference Materials (CRMs) developed in accordance with the present invention, the absolute molecular density in organic thin layers and the density of functional groups in organic thin layers can be determined without the absolute quantification by means of MEIS measurement.

While the present invention has been described with respect to the specific embodiments, it will be apparent to those skilled in the art that various changes and modifications may be made without departing from the spirit and scope of the invention as defined in the following claims.

The invention claimed is:
1. A quantification method of functional groups in an organic thin layer comprising:
   measuring an absolute quantity per unit area of an analysis reference material having functional groups included in a reference organic thin layer by means of medium energy ion scattering (MEIS) spectroscopy;

carrying out spectrometry for the same reference organic thin layer as in said measuring the absolute quantity per unit area, and thereby obtaining peak intensities of the functional groups in the reference organic thin layer;

carrying out the same spectrometry as in said carrying out the spectrometry for an organic thin layer to be analyzed having the same functional groups as those included in the analysis reference material of said measuring the absolute quantity per unit area, and thereby measuring peak intensities of the functional groups with unknown quantity; and comparing the peak intensities of the functional groups measured in said carrying out the spectrometry with respect to the absolute quantity of the analysis reference material in said measuring the absolute quantity per unit area, and thereby determining the absolute quantity per unit area of the functional groups with unknown quantity in the organic thin layer to be analyzed measured in said measuring the peak intensities of the functional groups.

2. The quantification method of functional groups in an organic thin layer according to claim 1, wherein the reference organic thin layer is prepared by spin-coating organic thin layers with different concentrations, which are prepared from an analyte including the analysis reference material at various concentrations, on a monocrystalline silica substrate, a monocrystalline silicon substrate having a surface oxide layer or a monocrystalline silicon substrate.

3. The quantification method of functional groups in an organic thin layer according to claim 1, wherein the spectrometry is selected from a group consisting of X-ray photoelectron spectroscopy (XPS), Fourier transform-infrared (FT-IR) spectroscopy or time-of-flight secondary ion mass spectrometry (ToF-SIMS).

4. The quantification method of functional groups in an organic thin layer according to claim 1, wherein the measurement of the absolute quantity per unit area of the analysis reference material having functional groups included in the reference organic thin layer by means of MEIS comprises:

injecting protons ($H^+$) along a crystal direction of the reference organic thin layer on a predetermined area of the reference organic thin layer and detecting the energy and emission quantity of the scattered protons;

obtaining the areal density of elements based on the detected energy and emission quantity of the protons; and obtaining the density of the analysis reference material from the areal density of the elements included in the reference organic thin layer.

5. The quantification method of functional groups in an organic thin layer according to claim 4, wherein, in said obtaining the density of the analysis reference material, the areal density of elements included in the functional groups of the reference organic thin layer is obtained from the areal density of the analysis reference material.

6. A quantification method of functional groups in an organic thin layer comprising:

carrying out spectrometry for an organic thin layer to be analyzed and thereby obtaining peak intensities of functional groups with unknown quantity; and comparing the peak intensities of the functional groups with unknown quantity obtained in said obtaining the peak intensities of the functional groups with respect to an absolute quantity per unit area of functional groups included in a reference organic thin layer, which is obtained by comparing an absolute quantity per unit area of an analysis reference material having functional groups included in the reference organic thin layer measured by means of MEIS with peak intensities of the functional groups in the reference organic thin layer measured by means of spectrometry, and thereby determining the absolute quantity per unit area of the functional groups in the organic thin layer to be analyzed.

7. The quantification method of functional groups in an organic thin layer according to claim 6, wherein the reference organic thin layer is prepared by spin-coating organic thin layers with different concentrations, which are prepared from an analyte including the analysis reference material at various concentrations, on a monocrystalline silica substrate, a monocrystalline silicon substrate having a surface oxide layer or a monocrystalline silicon substrate.

8. The quantification method of functional groups in an organic thin layer according to claim 6, wherein the spectrometry is selected from a group consisting of X-ray photoelectron spectroscopy (XPS), Fourier transform-infrared (FT-IR) spectroscopy or time-of-flight secondary ion mass spectrometry (ToF-SIMS).

9. The quantification method of functional groups in an organic thin layer according to claim 6, wherein the measurement of the absolute quantity per unit area of the analysis reference material having functional groups included in the reference organic thin layer by means of MEIS comprises:

injecting protons ($H^+$) along a crystal direction of the reference organic thin layer on a predetermined area of the reference organic thin layer and detecting the energy and emission quantity of the scattered protons;

obtaining the areal density of elements based on the detected energy and emission quantity of the protons; and obtaining the density of the analysis reference material from the areal density of the elements included in the reference organic thin layer.

10. The quantification method of functional groups in an organic thin layer according to claim 9, wherein, in said obtaining the density of the analysis reference material, the areal density of elements included in the functional groups of the reference organic thin layer is obtained from the areal density of the analysis reference material.

* * * * *